United States Patent
Suematsu

(10) Patent No.: US 9,760,984 B2
(45) Date of Patent: Sep. 12, 2017

(54) CONTROL UNIT FOR GENERATING TIMING SIGNAL FOR IMAGING UNIT IN INSPECTION SYSTEM AND METHOD FOR SENDING OUT TIMING SIGNAL TO IMAGING UNIT

(71) Applicant: EBARA CORPORATION, Tokyo (JP)

(72) Inventor: Kenichi Suematsu, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 79 days.

(21) Appl. No.: 14/680,286

(22) Filed: Apr. 7, 2015

(65) Prior Publication Data
US 2015/0285746 A1    Oct. 8, 2015

(30) Foreign Application Priority Data

Apr. 7, 2014  (JP) .................................. 2014-078565

(51) Int. Cl.
*G01N 21/88* (2006.01)
*G06T 7/00* (2017.01)
(Continued)

(52) U.S. Cl.
CPC ....... *G06T 7/0004* (2013.01); *G01N 23/2251* (2013.01); *H01J 37/20* (2013.01);
(Continued)

(58) Field of Classification Search
CPC .................. G06T 7/0004; H01J 37/20; H01J 2237/20292; H01J 2237/24592; H01J 37/28; G01N 23/2251; G01N 2223/6116
See application file for complete search history.

(56) References Cited

U.S. PATENT DOCUMENTS 4,775,236 A * 10/1988 Cohen ................. G01B 11/105
  356/640
5,276,451 A * 1/1994 Odagawa ............... G01S 19/49
  342/357.32

(Continued)

FOREIGN PATENT DOCUMENTS

JP    H11-132975 A    5/1999
JP    2007-48686 A    2/2007
WO    02/01596 A1    1/2002

*Primary Examiner* — Jay Patel
*Assistant Examiner* — Joseph Suh
(74) *Attorney, Agent, or Firm* — Pearne & Gordon LLP

(57) ABSTRACT

A control unit for generating a timing signal for an imaging unit in an inspection system in which an image of an inspection target object is captured by the imaging unit while the inspection target object is caused to travel in a predetermined direction includes a traveling distance determination section configured to detect a traveling distance of the inspection target object based on a count value acquired as an integer value from a laser interferometer provided in the inspection system for detecting a traveling distance of the inspection target object, and configured to determine whether the detected traveling distance reaches a threshold, and a timing signal generation section configured to generate a timing signal when it is determined that the detected traveling distance reaches the threshold. The traveling distance determination section executes the determination by using a plurality of values selectively as the threshold.

9 Claims, 10 Drawing Sheets

(51) Int. Cl.
*G01N 23/225* (2006.01)
*H01J 37/20* (2006.01)
*H01J 37/28* (2006.01)

(52) U.S. Cl.
CPC ....... *G01N 2223/6116* (2013.01); *H01J 37/28* (2013.01); *H01J 2237/20292* (2013.01); *H01J 2237/24592* (2013.01)

(56) References Cited

U.S. PATENT DOCUMENTS

| | | | | |
|---|---|---|---|---|
| 5,699,145 | A * | 12/1997 | Makinouchi | G03F 7/70358 250/206 |
| 6,265,719 | B1 | 7/2001 | Yamazaki et al. | |
| 8,280,664 | B2 * | 10/2012 | Kimba | H01J 37/28 250/252.1 |
| 8,467,770 | B1 * | 6/2013 | Ben Ayed | H04L 63/107 455/41.1 |
| 2002/0028399 | A1 * | 3/2002 | Nakasuji | G01N 23/225 430/30 |
| 2002/0040263 | A1 * | 4/2002 | Johnson | G01C 5/005 701/17 |
| 2003/0090582 | A1 * | 5/2003 | Shimokawa | H04N 5/2353 348/297 |
| 2004/0232370 | A1 * | 11/2004 | Parsons | E03C 1/057 251/129.04 |
| 2007/0164234 | A1 * | 7/2007 | Tsuji | G03F 7/70775 250/491.1 |
| 2009/0121915 | A1 * | 5/2009 | Randler | G01S 13/345 342/70 |
| 2009/0224151 | A1 | 9/2009 | Hatakeyama et al. | |
| 2010/0220337 | A1 * | 9/2010 | Lee | G01B 11/0608 356/516 |
| 2010/0282956 | A1 * | 11/2010 | Kimba | H01J 37/28 250/252.1 |
| 2010/0296039 | A1 * | 11/2010 | Zhao | G02F 1/133753 349/129 |
| 2012/0328197 | A1 * | 12/2012 | Sanderson | G06K 9/6227 382/191 |
| 2013/0342368 | A1 * | 12/2013 | Nathanson | G07C 5/008 340/903 |

* cited by examiner

CONTROL UNIT FOR GENERATING TIMING SIGNAL FOR IMAGING UNIT IN INSPECTION SYSTEM AND METHOD FOR SENDING OUT TIMING SIGNAL TO IMAGING UNIT

TECHNICAL FIELD

The present invention relates to a control technique for generating an imaging unit timing signal in an inspection system which includes an imaging unit.

BACKGROUND ART

Inspection systems are widely known for inspecting a pattern or the like which is formed on a surface of an inspection target object. In these inspection systems secondary charged particles which is obtained according to characteristic conditions of the surface of the inspection target object by irradiating a surface of an inspection target object such as a wafer with charged particles or electromagnetic waves are detected by an imaging unit, and the pattern or the like formed on the surface of the inspection target object is inspected by using image data generated based on the results of the detection (for example, refer to International Patent Publication No. 2002/001596, Japanese Patent Application Public Disclosure No. 2007-48686, and Japanese Patent Application Public Disclosure No. H11-132975). In many of these inspection systems, a form is adopted in which an inspection target object are irradiated with charged particles or electromagnetic waves while the traveling stage on which the inspection target object is held is caused to move and a quantity of light is taken in from an imaging unit every time the traveling stage moves a distance corresponding to one pixel of a captured image (an image captured by an imaging element) (a distance in which a traveling distance of an image projected on to the imaging element is one pixel and which is determined by the magnification of an optical system) to thereby generate image data. An example of a unit by which the size of one pixel of a captured image is expressed on an object surface of an imaging target object is nm/pix. In the case of one pixel corresponding to 50 nm on the object surface, it is expressed as 50 nm/pix. In this case, a stage traveling distance corresponding to one pixel is 50 nm. A timing at which the quantity of light is taken in is determined by a timing signal which is inputted into the imaging unit.

In this inspection system, in general, it is detected by using a laser interferometer that the traveling stage moves the distance corresponding to one pixel of the captured image. Specifically, it is determined whether or not the traveling stage has moved the distance corresponding to one pixel by converting a count value which is obtained from the laser interferometer as an integer value into an actual distance. For example, in the event that the resolution of the laser interferometer is 0.61815562 nm/count and the distance corresponding to one pixel is 50 nm, an accurate count value which corresponds to the distance corresponding to one pixel is 80.8858 counts (=50/0.61815562). However, as described above, the count value is obtained as an integer value. Because of this, in the conventional inspection systems, 81 counts, which results from rounding off a decimal part of the accurate count value (values below the decimal point), is treated as the distance corresponding to one pixel.

SUMMARY

In the conventional inspection system, a minute positional error is generated every time the quantity of light is taken in from the imaging unit, that is, every time it is determined that the traveling stage has moved the distance corresponding to one pixel of the captured image. For example, in the specific example described above, since the distance corresponding to one pixel which is originally 80.8858 counts is treated as 81 counts, a positional error of 0.1142 count (corresponding to 0.07059 nm) is generated every time it is determined that the traveling stage has moved the distance corresponding to one pixel of the captured image. As is obvious from the calculation of the accurate count value, the generation of this positional error is attributed to the fact that the distance corresponding to one pixel is not the integral multiple of the resolution of the laser interferometer. Although the positional error is extremely minute, the positional error is accumulated every time the traveling stage moves the distance corresponding to one pixel of the captured image, and therefore, in the case of the traveling stage traveling a long distance, the positional error reaches a level that cannot be ignored. For example, when the traveling stage moves 100 mm, an image of 1,997,179 pixels (=100 mm/(81 counts*0.61815562 nm/count) is captured. As this occurs, a positional error of about 141 μm (1,997,179 pixels*0.07059 nm/pixel) is generated. This accumulated large positional error affects the inspection accuracy.

In view of the foregoing, it is preferable to restrict the accumulation of positional errors which result from the fact that the ratio of the distance corresponding to one pixel of the captured image to the resolution of the laser interferometer is not the integral multiple. As a method for restricting the accumulation of such positional errors, it is considered to adjust the magnification of the optical system of the inspection system. For example, in the specific example described above, a method is considered of adjusting the magnification of the optical system of the inspection system so that the distance corresponding to one pixel of the captured image becomes 50.070605 (81 pixels*0.61815562 nm/count). However, a minute adjustment of magnification like this is difficult, and hence, it is preferable to restrict the accumulation of positional errors by using other methods.

According to one embodiment of the invention, provided is a control unit for generating a timing signal for an imaging unit in an inspection system in which an image of an inspection target object is captured by the imaging unit while the inspection target object is caused to travel in a predetermined direction. This control unit includes a traveling distance determination section configured to detect a traveling distance of the inspection target object based on a count value acquired as an integer value from a laser interferometer provided in the inspection system for detecting a traveling distance of the inspection target object, and configured to determine whether the detected traveling distance reaches a threshold; and a timing signal generation section configured to generate a timing signal when it is determined that the detected traveling distance reaches the threshold. The traveling distance determination section executes the determination by using a plurality of values selectively as the threshold.

DESCRIPTION OF EMBODIMENTS

Figure 1:
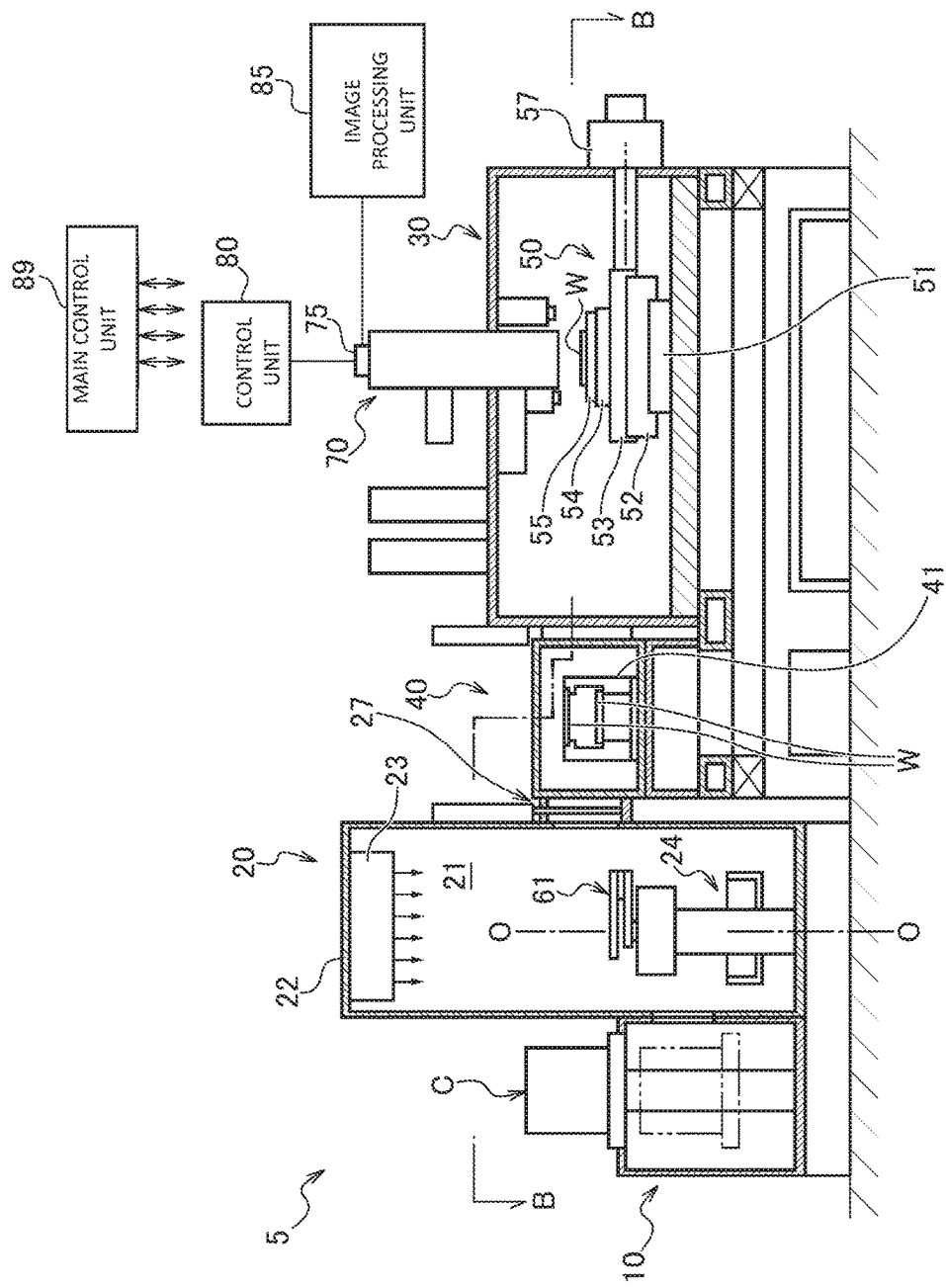
FIG. 1 is a schematic elevation view of an inspection system as an embodiment of the invention.

According to a first embodiment of the invention, provided is a control unit for generating a timing signal for an imaging unit in an inspection system in which an image of an inspection target object is captured by the imaging unit while the inspection target object is caused to travel in a predetermined direction. This control unit includes a traveling distance determination section configured to detect a traveling distance of the inspection target object based on a count value acquired as an integer value from a laser interferometer provided in the inspection system for detecting a traveling distance of the inspection target object, and configured to determine whether the detected traveling distance reaches a threshold; and a timing signal generation section configured to generate a timing signal when it is determined that the detected traveling distance reaches the threshold. The traveling distance determination section executes the determination by using a plurality of values selectively as the threshold.

According to this control unit, the plurality of values are used selectively as the threshold. In case a value which is larger than an accurate traveling distance of the inspection target object which is to correspond a timing at which a timing signal is generated, and a value smaller than the traveling distance are used as the plurality of values, it is possible to reduce the accumulation of positional errors which are caused by a difference between the accurate traveling distance of the inspection target object which is to correspond to the timing at which a timing signal is generated and a traveling distance of the inspection target object which is detected from a count value of the laser interferometer (and hence a threshold). In other words, there is no such situation in which a constant positional error is accumulated at all times as in a case where one threshold is used in a fixed fashion. Thus, the accumulation of positional errors is restricted which accumulation is caused by the fact that the ratio of the distance corresponding to one pixel of the captured image to the resolution of the laser interferometer for detecting the traveling distance of the inspection target object is not the integral multiple, thereby making it possible to inspect the inspection target object with good accuracy.

According to a second embodiment of the invention, in the first embodiment, the traveling distance determination section is configured to integrate a decimal part corresponding value, which corresponds to a decimal part of a converted count value which results from converting a distance corresponding to one pixel of an image captured by the imaging unit into the count value of the laser interferometer in such a way as to include the decimal part, according to the number of times the timing signal is generated by the timing signal generating section, and configured to switch the threshold to be selected between the plurality of values based on the integrated decimal part corresponding value. According to this embodiment, the integrated corresponding value corresponds to an amount of the accumulated positional errors, and therefore, it is possible to reduce the accumulated distance of positional errors by switching a value for the threshold before an accumulated distance of positional errors reaches a predetermined distance.

According to a third embodiment of the invention, in the second embodiment, the traveling distance determination section is configured to select a first value of the plurality of values when the integrated decimal part corresponding value is smaller than a predetermined value and is configured to select a second value of the plurality of values, the second value being larger than the first value, when the integrated decimal part corresponding value is equal to or larger than the predetermined value, and to subtract a value corresponding to a difference between the second value and the first value from the integrated decimal part corresponding value. According to this embodiment, when the total distance of accumulated positional errors does not reach the predetermined value, the first value which is relatively smaller is used as the threshold, and every time the total distance of accumulated positional errors exceeds an amount corresponding to the predetermined value, the second value which is relatively larger is used as the threshold, whereby the total distance of the accumulated positional errors is reduced. Namely, every time the accumulated positional error exceeds the amount corresponding to the predetermined value, the total distance of the accumulated positional errors is reduced, and therefore, there is no such situation in which the positional errors are accumulated to such an extent as to exceed the predetermined value largely. Additionally, the difference between the second value and the first value which corresponds to the positional error solved by the use of the second value as the threshold is subtracted from the integrated decimal port corresponding value, and therefore, the same process can also preferably be executed thereafter based on the remaining positional errors.

According to a fourth embodiment of the invention, in the third embodiment, the plurality of values consist of the first value and the second value, the predetermined value is a value by which whether the integrated decimal part corresponding value is carried up can be determined, the first value is a value corresponding to an integer part of the converted count value, and the second value is larger by value 1 than the first value. According to this embodiment, when the positional errors are accumulated by a distance corresponding to a value of 1 of the count value of the laser interferometer, the accumulated distance of positional errors is reduced, whereby the accumulated distance of positional errors can be kept to an extremely small value.

According to a fifth embodiment of the invention, in the first embodiment, the traveling distance determination section is configured to switch the threshold to be selected in a predetermined order which is associated with transmission of the timing signal by the timing signal generation section. According to this embodiment, the accumulation of positional errors can preferably be restricted by a simple logic.

According to a sixth embodiment of the invention, in the fifth embodiment, the traveling distance determination section is configured to switch the threshold from a first value to a second value, which differs from the first value, when the timing signal generation section generates the timing signal by a first predetermined number of times based on the first value as the threshold, and configured to switch the threshold from the second value to the first value when the timing signal generation section generates the timing signal by a second predetermined number of times based on the second value. According to this embodiment, no specific threshold selection order needs to be stored in the memory.

According to a seventh embodiment of the invention, an inspection system is provided. This inspection system includes the control unit according to anyone of the first to sixth embodiments, the imaging unit, a traveling unit configured to hold an inspection target object to cause the inspection target object to travel in a predetermined direction, and the laser interferometer. According to this inspection system, the same technical effect as those of the first to sixth embodiments can be provided.

According to an eighth embodiment of the invention, there is provided a method for sending out a timing signal to an imaging unit in an inspection system in which an image of an inspection target object is captured by the imaging unit while the inspection target object is caused to travel in a predetermined direction. This method includes detecting a traveling distance of the inspection target object based on a count value which is acquired as an integer value from a laser interferometer for detecting the traveling distance of the inspection target object to determine whether the detected traveling distance reaches a threshold, and sending out the timing signal to the imaging unit when it is determined that the detected traveling distance reaches the threshold. The threshold is switched between a plurality of values selectively. According to this method, the same technical effect as that provided by the first embodiment can be provided. It is possible to add any of the second to sixth embodiments to the eighth embodiment.

According to a ninth embodiment of the invention, there is provided a control unit for generating a timing signal for an imaging unit in an inspection system in which an image of an inspection target object is captured by the imaging unit while the inspection target object is caused to travel in a predetermined direction The control unit includes a timing signal generation section configured to generate the timing signal when it is determined that the traveling distance reaches a predetermined distance based on a count value which is acquired as an integer value from a laser interferometer provided in the inspection system for detecting a traveling distance of the inspection target object, and a correcting section configured to correct an error in relation to the predetermined distance which is caused by the fact that a ratio of a distance corresponding one pixel of a captured image to a resolution of the laser interferometer is not an integral multiple and which is accumulated every time the timing signal is generated. According to this embodiment, the same technical effect as that provided by the first embodiment can be provided.

In addition to the forms which have been described heretofore, the invention can be realized in various forms such as a program for transmitting a timing signal to the imaging unit, a storage medium on which the program is recorded so as to be read by a computer. Hereinafter, the above-mentioned embodiments will be described by reference to more detailed embodiments.

A. First Embodiment

Figure 2:
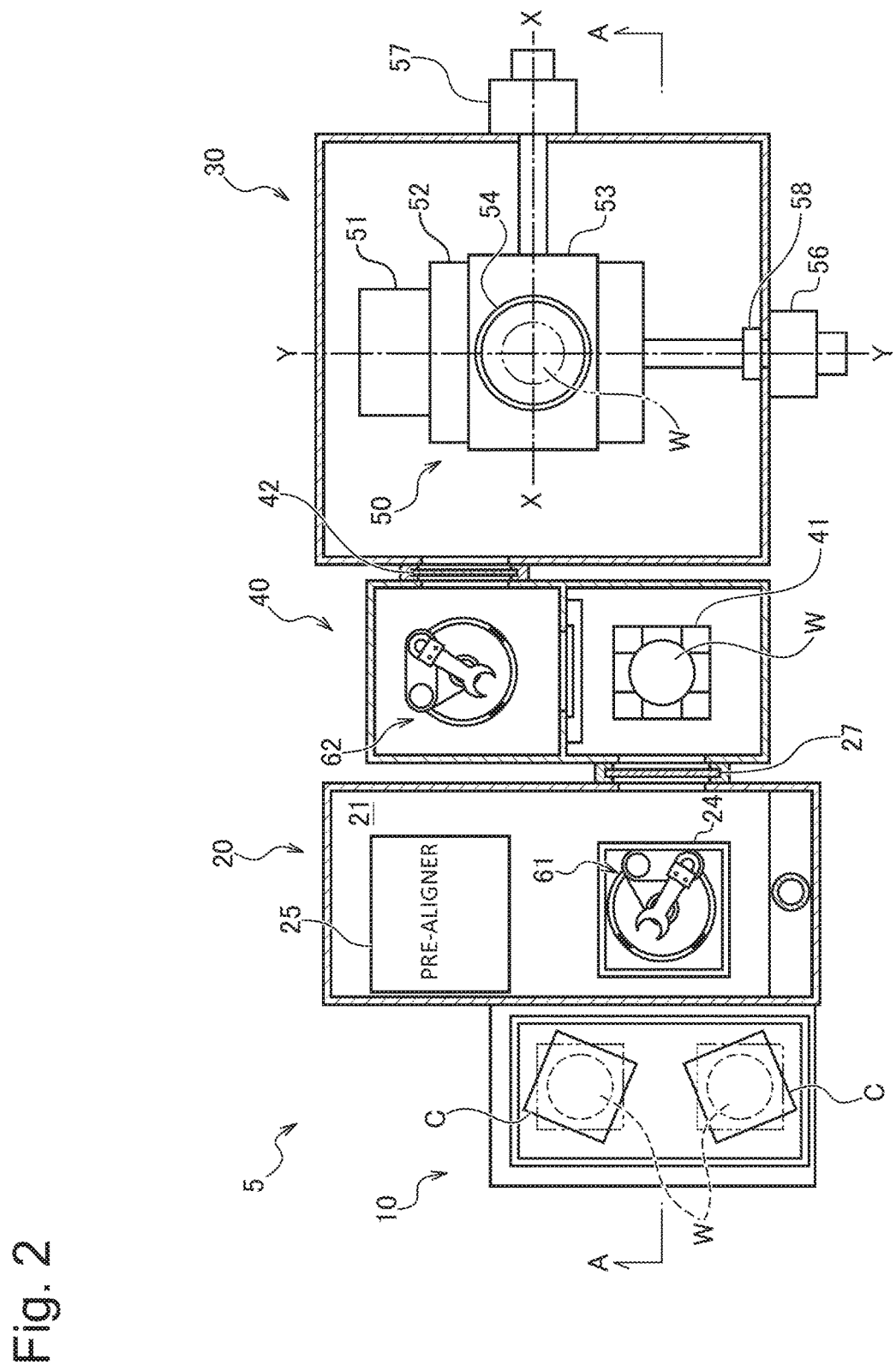
FIG. 2 is a schematic plan view of the inspection system shown in FIG. 1.

FIGS. 1 and 2 show a schematic configuration of a semiconductor inspection system (hereinafter, referred to simply as an inspection system) 5 as an embodiment of an inspection system of the invention. FIG. 1 is a schematic elevation view (as viewed in a direction indicated by arrows A-A in FIG. 2) of the inspection system 5, and FIG. 2 is a schematic plan view (as viewed in a direction indicated by arrows B-B in FIG. 1) of the inspection system 5. The inspection system 5 is a system for inspecting a failure of a pattern formed on a surface of an inspection target object, the presence of a foreign matter on the surface of the inspection target object or the like. Semiconductor wafer, exposing mask, EUV mask, nanoimprinting mask (and template), optical element substrate, optical circuit board and the like can be raised as examples of the inspection target object. As the foreign matter, for example, a particle, a cleaning residual (an organic matter), a reaction produce on the surface and the like can be raised. The foreign matter includes, for example, an insulating matter, a conductive matter, a semiconductor material or a composite thereof. In the following description, the inspection system 5 will be described as being used to inspect a semiconductor wafer (hereinafter, also referred to simply as a wafer W). A wafer is inspected in a semiconductor fabrication process after the wafer is treated or in the middle of treatment of the wafer. For example, an inspection is carried out on a wafer in a film-formed wafer, a CMP treated or ion poured wafer, a wafer on a surface of which a wiring pattern is formed, a wafer on which a wiring patter has not yet been formed, and the like.

As shown in FIG. 1, the inspection system 5 includes a cassette holder 10, a mini-environment apparatus 20, a main housing 30, a loader housing 40, a stage unit 50, an electron optical unit 70, a control unit 80, an image processing unit 85, and a main control unit 89. As shown in FIGS. 1 and 2, the cassette holder 10 is configured to hold a plurality of (two in FIG. 2) cassettes C. A plurality of wafers W as inspection target objects are accommodated in the cassette C in such a way as to be arranged parallel in a vertical direction. In this embodiment, the cassette holder 10 is configured so that cassettes C can automatically be set in positions indicated by chain lines in FIG. 2 on a cassette elevating table. The cassettes C set in the cassette holder 10 are turned automatically to a position indicated by a solid line in FIG. 2, that is, a position where the cassette C is oriented to a turning axis O-O (refer to FIG. 1) of a first transfer unit 61 in the mini-environment apparatus 20, which will be described later.

As shown in FIGS. 1 and 2, the mini-environment apparatus 20 includes a housing 22, a gas circulation unit 23, an exhaust unit 24, and a pre-aligner 25. A mini-environment space 21 is formed in an interior of the housing 22, and the atmosphere in the mini-environment space 21 is controlled. The first transfer unit 61 is placed within the mini-environment space 21. The gas circulation unit 23 circulates a clean gas (here, air) within the mini-environment space 21 to control the atmosphere therein. The exhaust unit 24 recovers part of air supplied to the interior of the mini-environment space 21 and exhausts it to an exterior of the housing 22. The pre-aligner 25 roughly positions wafers.

The first transfer unit 61 is placed within the mini-environment space 21. This first transfer unit 61 includes a multi-joint arm configured to turn about the axis O-O. This arm is configured to extend and contract in a radial direction. A gripping device for gripping a wafer W such as a mechanical chuck, a vacuum chuck or an electrostatic chuck is provided at a distal end of the arm. The arm can move vertically. The first transfer unit 61 grips on a required wafer W of a plurality of wafers held in the cassette holder 10 and transfers the wafer W to a wafer rack 41 in the loader housing 40, which will be described later.

As shown in FIGS. 1 and 2, the wafer rack 41 and a second transfer unit 62 are placed in an interior of the loader housing 40. The housing 22 of the mini-environment apparatus 20 and the loader housing 40 are divided by a shutter unit 27, and the shutter unit 27 is opened only when wafers W are transferred from the housing 20 to the loader housing 40. The wafer rack 41 supports a plurality of (two in FIG. 1) wafers W horizontally while the wafers W are spaced apart from each other vertically. The second transfer unit 62 has basically the same configuration as that of the first transfer unit described above. The second transfer unit 62 transfers wafers W between the wafer rack 41 and a holder 55 of the stage unit 50, which will be described later. The atmosphere in the interior of the loader housing 40 is controlled to be in a high vacuum condition (a degree of vacuum of $10^{-5}$ to $10^{-6}$ Pa), and an inert gas (for example, dried pure nitrogen) is filled thereinto.

As shown in FIGS. 1 and 2, the stage unit 50 is provided in the main housing 30 as an example of a traveling unit which carries a wafer W. The stage unit 50 includes a fixed table 51 disposed on a bottom wall, a Y table 52 which moves in a Y direction on the fixed table, an X table 53 which moves in an X direction on the Y table, a rotary table 54 which can rotate on the X table, and the holder 55 disposed on the rotary table 54. The Y table 52 is moved in the Y direction by a servo motor 56 which is an actuator provided outside the main housing 30. The X table 53 is moved in the X direction by a servo motor 57 which is an actuator provided outside the main housing 30. The holder 55 holds a wafer W on a resting surface thereof in a releasable fashion with a mechanical chuck or an electrostatic chuck. A traveling distance in the Y direction of the wafer W held by the holder 55 is detected by a laser interferometer 58.

The laser interferometer 58 is a laser interference distance measuring device which utilizes the principle of an interferometer. In FIGS. 1 and 2, the position of the laser interferometer 58 is shown schematically. For example, the laser interferometer 58 irradiates a mirror plate fixed to the Y table 52 (or the holder 55) with a laser beam which is, and measures the coordinate of the wafer W (strictly speaking, the coordinate of the Y table 52 or the holder 55) based on a phase difference between an incident wave of the laser and a reflected wave from the mirror plate by the laser interferometer, whereby a traveling distance of the wafer W is detected. The laser interferometer 58 may be provided inside or outside the main housing 30. Additionally, the laser interferometer 58 may be provided in a position spaced away from the main housing 30 by being connected to an optical pickup provided on an optical path of the laser beam by way of an optical cable. A count value CV can be acquired from the laser interferometer as a value representing the detected coordinates of the wafer W. This count value CV is acquired as an integer value. A distance corresponding to a value of 1 of the count value CV depends on the resolution of the laser interferometer 58, and this value of 1 corresponds, for example, to 0.61815562 nm.

The electron optical unit 70 irradiates a wafer W traveling in the Y direction (refer to FIG. 2) with a beam of charged particles and detects a quantity of secondary charged particles obtained by the irradiation. As an alternative form, the electron optical unit 70 may irradiate the wafer W with electromagnetic waves in place of the charged particles to detect secondary electromagnetic waves obtained by the irradiation. The wafer W is caused to travel by the stage unit 50. The control unit 80 outputs a TDI clock (transfer clock) as a timing signal to a TDI camera 75 provided in the electron optical unit 70 to control the operation of the TDI camera 75. The electron optical unit 70 and the control unit 80 will be described in detail later. The image processing unit 85 generates image data based on the quantity of secondary charged particles detected by the electron optical unit 70. The image data so generated has a luminance value as a gradation value.

The image data generated by the image processing unit 85 is used to inspect a pattern formed on a surface of the wafer W for failure or presence of foreign matters by an arbitrary method. This inspection may be executed automatically by using an information processing unit. For example, the information processing unit may detect an area where the luminance value is higher than a threshold or execute a pattern matching between the generated image data and reference image data prepared in advance. Alternatively, an inspector may execute an inspection based on an image produced by the image data or a gradation value of each pixel of the image data.

The main control unit 89 controls the whole operation of the inspection system 5. For example, the main control unit 89 sends out a traveling command to the stage unit 50 so that the stage unit 50 causes the holder 55 which holds the wafer W to travel in the Y direction at a predetermined traveling speed. The main control unit 89 may include a memory and a CPU to realize the required functions by executing programs stored in advance. Alternatively, the main control unit 89 may realize at least part of the required functions by a hardware circuit prepared exclusively therefor, in addition to or in place of realizing it by software.

Figure 3:
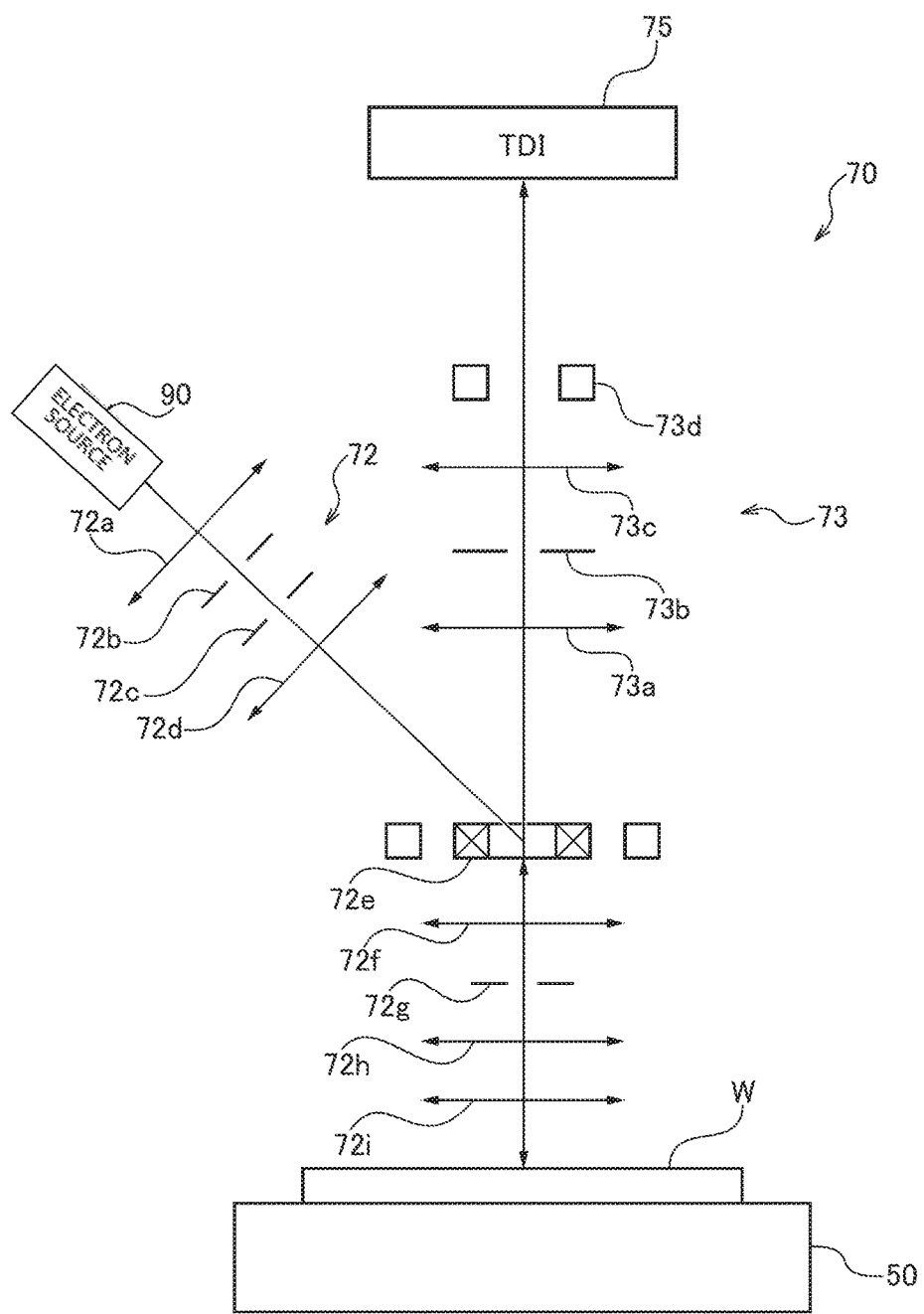
FIG. 3 is a diagram depicting a schematic configuration of an electronic optical unit.

FIG. 3 shows a schematic configuration of the electron optical unit 70. In this embodiment, the electron optical unit 70 is a mapping projection type electron microscope which simultaneously irradiates a wide surface of an inspection target object with electron beams at one time and detects at one time quantities of secondary charged particles obtained by the irradiation. However, the electron optical unit 70 may be a different type of electron microscope such as a scanning electron microscope which scans finely throttled electron beans over a surface of an inspection target object and detects quantities of the obtained secondary charged particles by pixel corresponding to the diameter of the electron beam. As shown in the figure, the electron optical unit 70 includes a primary optical system 72, a secondary optical system 73 and the TDI camera 75. The primary optical system 72 generates a beam of charged particles to irradiate the wafer W held by the holder 55. This primary optical system 72 includes an electron source 90, lenses 72a, 72d, apertures 72b, 72c, an ExB filter 72e, lenses 72f, 72h, 72i, and an aperture 72g.

Secondary charged particles representing or corresponding to a condition (a pattern formed condition, a foreign matter adhering condition or the like) on the surface of the wafer W are obtained by irradiating the wafer W with charged particles. In this specification, the secondary charged particle is anyone of a secondary emitted electron, a mirror electron and a photoelectron or a mixture thereof. The secondary emitted electron is anyone of a secondary electron, a reflection electron and a backscattered electron or a mixture of at least two of these electrons. When irradiating the surface of the wafer W with charged particles in the form of an electron beam or the like, secondary emitted electrons are generated as a result of the charged particles colliding against the surface of the wafer W. When irradiating the surface of the wafer W with charged particles in the form of an electron beam or the like, mirror electrons are generated as a result of the charged particles being reflected near the surface of the wafer W without colliding against the surface of the wafer W. When irradiating the surface of the wafer W with electromagnetic waves, photoelectrons are generated from the surface of the wafer W.

The lenses 72a, 72d and the apertures 72b, 72c shape an electron beam generated by the electron source 90 and controls the direction of the electron beam so that the electron beam is guided to the ExB filter 72e so as to enter it from an oblique direction. The electron beam which enters the ExB filter 72e is affected by a Lorentz force resulting from the magnetic field and the electric field and is then deflected vertically downwards to be guided towards the wafer W via the lenses 72f, 72h, 72i and the aperture 72g. The lenses 72f, 72h, 72i control the direction of the electron beam and decelerate the electron beam as required to adjust landing energy.

A foreign matter on the wafer W is charged up by irradiating the wafer W with an electron beam, whereby part of electrons which are about to fall on the wafer W are sprung back without contacting the wafer W. This guides mirror electrons to the TDI camera 75 via the secondary optical system 73. Additionally, another part of the electrons which are about to fall on the wafer W are allowed to fall thereon to contact the wafer W, whereby secondary charged electrons are emitted.

The secondary charged particles obtained by the irradiation of the electron beam (here, the mirror electrons and secondary emitted electrons) pass through the objective lens 72i, lens 72h, the aperture 72g, the lens 72f and the ExB filter 72e again and are then guided to the secondary optical system 73. The secondary optical system 73 guides the secondary charged particles obtained by the irradiation of the electron beam to the TDI camera 75. The secondary optical system 73 includes lenses 73a, 73c, an NA aperture 73b and an aligner 73d. In the secondary optical system 73, the secondary charged particles are collected as they pass through the lens 73a, the NA aperture 73b and the lens 73c and are shaped by the aligner 73d. The NA aperture 73b plays a role of adjusting the transmissivity and aberration of the secondary system.

The TDI camera 75 includes imaging elements arranged in a predetermined number of stages (a plurality of stages) in the Y direction and detects a quantity of secondary charged particles guided by the secondary optical system 73. In this embodiment, in the TDI camera 75, the imaging elements are also arranged in the X direction. The detection at the TDI camera 75 is executed so that the wafer W is irradiated with an electron beam while the wafer W is being caused to travel along the Y direction by the traveling stage 50, and a quantity of secondary charged particles (electric charges) obtained by the irradiation is integrated in the Y direction by the number of stages of imaging elements arranged in the Y direction through time delay integration. The traveling direction of the wafer W and the integrating direction by the TDI camera 75 are the same. The quantity of secondary charged particles is integrated stage by stage every time a TDI clock is inputted into the TDI camera 75. In other words, electric charges accumulated in one pixel of the TDI camera 75 are transferred to an adjacent pixel in the Y direction every time a TDI clock is inputted into the TDI camera 75. Then, a detected quantity in which the quantity of secondary charged particles is integrated by the number of stages of imaging elements arranged in the Y direction, that is, a detected quantity in which the quantity of secondary charged particles is integrated to the final stage is transferred to the image processing unit 85 every time a TDI clock is inputted into the TDI camera 75. The integrating direction of the TDI camera 75 is not limited to the Y direction and hence may be the X direction. As this occurs, the wafer W is caused to travel in the X direction.

Figure 4:
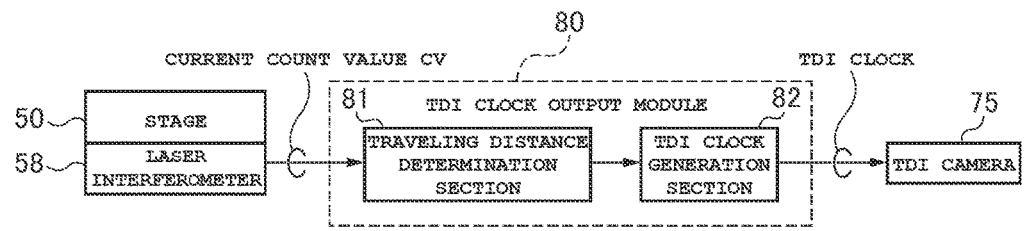
FIG. 4 is a functional block diagram showing a configuration in which a control unit outputs a TDI clock signal as a timing signal.
Figure 5:
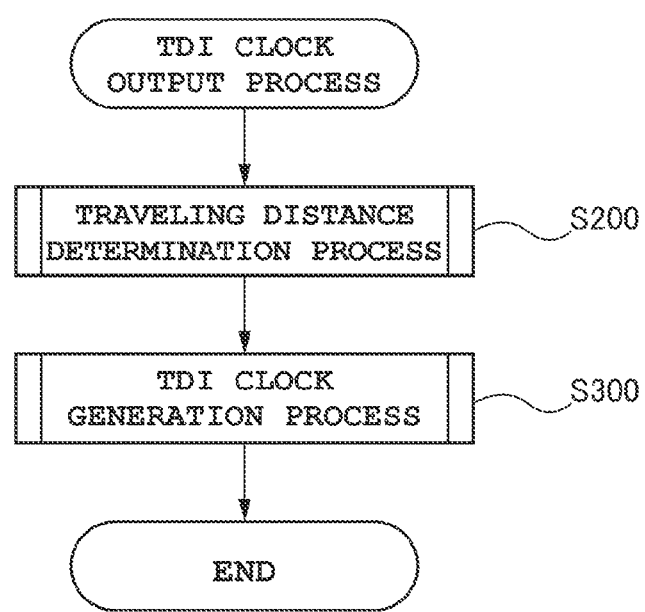
FIG. 5 is a flowchart showing a flow of TDI clock signal output process.

FIG. 4 is a functional block diagram showing a configuration in which the control unit 80 outputs a TDI clock signal to the TDI camera 75. FIG. 5 is a flowchart showing a flow of a TDI clock output process executed by the control unit 80. As shown in FIG. 4, the control unit 80 is configured as a TDI clock output module and includes a traveling distance determination section 81 and a TDI clock generation section 82, as shown in the figure. The TDI clock output process is executed repeatedly continuously within a period of time when the wafer W is irradiated with an electron beam while the wafer W is being caused to travel by the stage unit 50, and a quantity of secondary charged particles obtained by the irradiation is detected by the TDI camera 75.

As shown in FIG. 5, in the TDI clock output process, the control unit 80 first executes a traveling distance determination process as a process executed by the traveling distance determination section 81 (step S200). This process is a process in which a current count value CV is acquired from the laser interferometer 58, a traveling distance of the wafer W is detected based on the acquired count value CV, and it is determined whether the detected traveling distance reaches a threshold ThPix, as shown in FIG. 4. Next, as shown in FIG. 5, the control unit 80 executes a TDI clock generation process (step S300) as a process executed by the TDI clock generation section 82. This process is a process in which when it is determined by the traveling distance determination section 81 that the detected traveling distance reaches the threshold ThPix, as shown in FIG. 4, the control unit 80 generates a TDI clock signal to output it to the TDI camera 75. By executing this TDI clock output process, the control unit 80 outputs the TDI clock signal to the TDI camera 75 every time it is determined that the wafer W has traveled a distance corresponding to one pixel of the TDI camera 75 in the Y direction. The control unit 80 may include a memory and a CPU to realize the functions of the traveling distance determination section 81 and the TDI clock generation section 82 by executing a program stored in advance. Alternatively, in addition to or in place of realizing those functions by the software, the control unit 80 may realize at least part of those functions by using a hardware circuit prepared exclusively therefor. Hereinafter, the traveling distance determination process and the TDI clock generation process of this embodiment will be described in detail.

Figure 6:
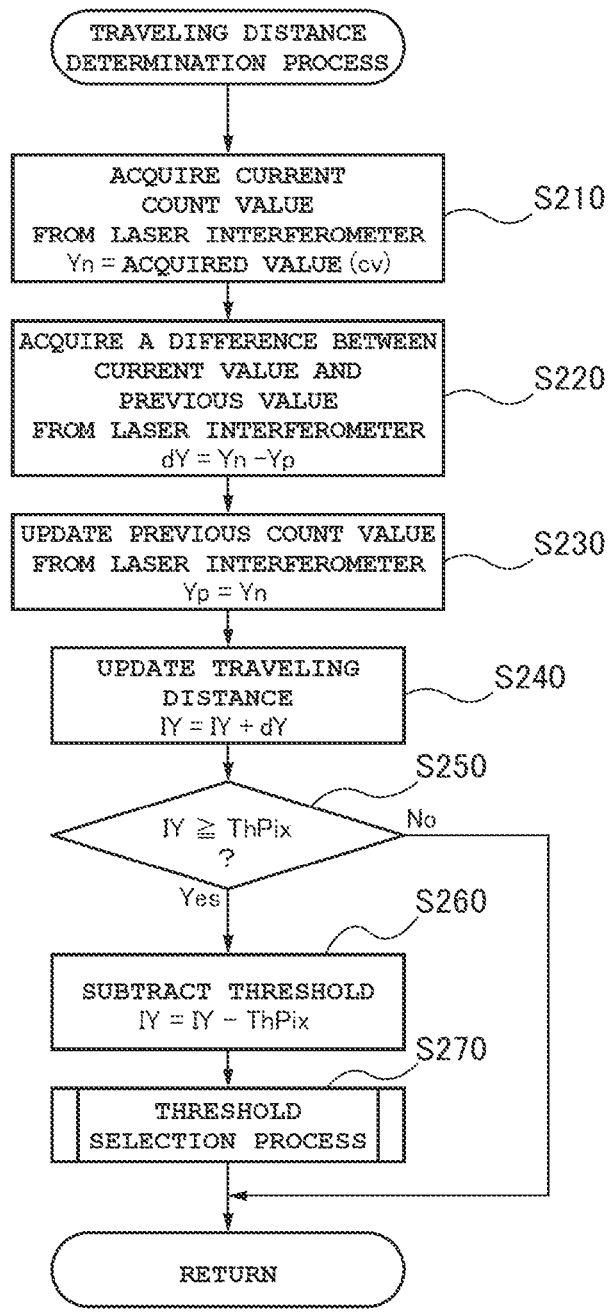
FIG. 6 is a flowchart showing a flow of traveling distance determination process.

FIG. 6 is a flowchart showing a flow of the traveling distance determination process (step S200 shown in FIG. 5). When this process is initiated, the control unit 80 first acquires a current count value CV (also, referred to as a current count value Yn) from the laser interferometer 58 (step S210). Next, the control unit 80 calculates a difference dY (=Yn−Yp) between the current count value Yn and the count value CV (also, referred to as the previous count value Yp) which is acquired from the laser interferometer 58 in the previous step S210 executed just before the current process (step S220). The previous count value Yp is stored in the memory of the control unit 80. When the traveling distance determination process is executed for the first time, the previous count value Yp is a value of 0 (zero).

Next, the control unit 80 updates the previous count value Yp (step S230). Namely, the control unit 80 stores the current count value Yn as the previous count value Yp in preparation for step S220 in a traveling distance determination process to be executed next time. Next, the control unit 80 adds the difference dY calculated in step S220 described above to the current traveling distance IY to update the traveling distance IY (step S240). The traveling distance IY is a traveling distance of the wafer W which is detected based on the count value CV acquired from the laser interferometer 58, and is expressed by an integer value of which a minimum unit is a value of 1 of the count value CV. When the traveling distance determination process is executed for the first time, the traveling distance IY before it is updated is a value of 0.

Next, the control unit 80 compares the updated traveling distance IY with the threshold ThPix to determine whether the traveling distance IY is equal to or larger than the threshold ThPix (step S250). In this step S250, it is determined whether the control unit 80 reaches a timing to generate a TDI clock signal, that is, whether the wafer W travels a distance corresponding to one pixel of an image captured by the TDI camera 75. Because of this, the threshold ThPix is set based on the distance corresponding to one pixel of an image captured by the TDI camera 75. In this embodiment, as will be described later, two predetermined values are used selectively as the threshold ThPix.

If the traveling distance IY is determined to be equal to or larger than the threshold ThPix as a result of the determination (S250: Yes), the control unit 80 subtracts the threshold ThPix from the traveling distance IY (step S260). This allows the value of "IY−ThPix" calculated this time to be used as a traveling distance IY in step S310 in the TDI clock generation process, which will be described later. Also, in step S240 in the traveling distance determination process to be executed next time, the value of "IY−ThPix" calculated this time is used as a traveling distance IY. By executing these operations, a TDI clock signal is generated in the TDI clock generation process, which will be described later, and the value of the traveling distance IY is reset in preparation for step S240 in the traveling distance determination process to be executed next time. Resetting the value of IY not to "0" but to "IY−ThPix" restricts the accumulation of positional errors. Specifically, the determination in step S250 may be made at a timing of IY=ThPix or at a timing of IY=ThPix+α (α is a natural number), depending upon the timing at which the count value CV is acquired from the laser interferometer 58. According to step S260 in this embodiment, in case the determination in step S250 is made at the timing of IY=ThPix+α, a positional error corresponding to value α can be reflected to next traveling distance determination process.

Next, the control unit 80 executes a threshold selection process (step S270). The threshold selection process is a process (to be described in detail later) of selecting a value to be used as the threshold ThPix from a plurality of values (in this embodiment, two values of Ni and Ni+1). The value selected in step S270 is used in step S250 of the traveling distance determination process to be executed next time. In this embodiment, the threshold is set to ThPix=Ni by default. However, when a traveling distance determination process is executed for the first time, the value of the threshold ThPix may be determined by executing a threshold selection process, which will be described later, prior to step S210. When the threshold selection process is completed, the control unit 80 returns the process to the TDI clock output process. On the other hand, if the traveling distance IY is smaller than the threshold ThPix as a result of the determination (S250: No), the control unit 80 returns the process to the TDI clock output process without executing the threshold selection process.

Figure 7:
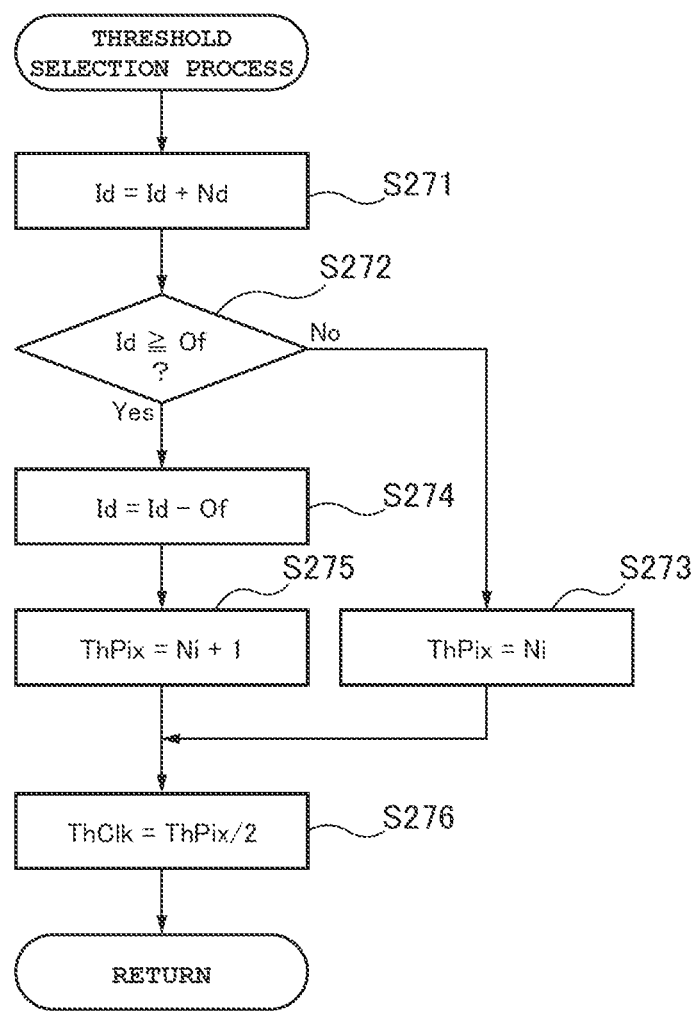
FIG. 7 is a flowchart showing a flow of threshold selection process.

FIG. 7 is a flowchart showing a flow of the threshold selection process (step S270 shown in FIG. 6). In the following description, an integer number part value Ni means a value of an integer number part of a value resulting from converting accurately the distance (in the traveling direction of the stage unit 50, that is, the Y direction) which corresponds to one pixel of an image captured by the TDI camera 75 into the count value CV (hereinafter, also referred to as a converted count value). A decimal number part corresponding value Nd (hereinafter, also referred to simply as a decimal number part value Nd) means a value corresponding to a decimal number part of the converted count value. The "value corresponding to the decimal number part" may be a value of a decimal number part itself or a value resulting from multiplying a value of a decimal number part itself by a predetermined coefficient (for example, a coefficient for converting a value of a decimal part to an integer number). For example, in the case of the converted count value being 80.8858 counts, the integer number part value Ni is a value of 80. In this case, the decimal number part value Nd is a value of 0.8858 when the "value corresponding to the decimal number part" is a value of a decimal number part itself. When the "value corresponding to the decimal number part" is a value resulting from multiplying a value of a decimal number part itself by a predetermined coefficient, the decimal number part value Nd is, for example, a value of 8858 (in this case, the coefficient is a value of 10000). By converting the decimal number part value Nd into the integer number in this way, it becomes easy to treat the number. In this embodiment, the "value corresponding to the decimal number part" is the value resulting from converting the decimal number part itself into the integer number in the way described above.

In the following description, a decimal number part corresponding integrated value Id (hereinafter, also referred to simply as an integrated value Id) means a value resulting from integrating the decimal number part value Nd every time the control unit 80 outputs a TDI clock signal. As has been described above, whether a TDI clock signal is to be generated, in other words, whether the wafer W travels the distance corresponding to one pixel is determined in step S240 by using the traveling distance IY which is the integer value, and therefore, in reality, even though the determination in step S250 is made at the timing of IY=ThPix, a positional error not greater than a value below the decimal point is generated. A value corresponding to the positional error not greater than a value below the decimal point is integrated every time the control unit 80 outputs a TDI clock signal, and the resulting integrated value is the integrated value Id.

As shown in FIG. 7, when the threshold selection process is initiated, the control unit 80 first updates the integrated value Id (step S271). Namely, a value resulting from adding the decimal number part value Nd to the integrated value Id is calculated as a new integrated value Id. When the threshold selection process is executed for the first time, the integrated value Id prior to the update is a value of 0. For example, in the case of the example described above (namely, in the case of Nd=8858), after it is updated, the integrated value Id is updated from the value of 0 to a value of 8858.

Next, the control unit 80 determines whether the updated integrated value Id is equal to or greater than a determination threshold Of (step S272). In this embodiment, the determination threshold Of is a value by which whether the integrated value Id is carried up by the update (integration) can be determined. Namely, the determination threshold Of is a value which is larger by one digit place than the decimal number part value Nd. It is preferable that this value is set to a minimum value in values which are larger by one digit place than the decimal number part value Nd to enhance the determination accuracy. For example, in the case of the decimal number part Nd being the value of 8858, the determination threshold Of is a value of 10000.

If the integrated value Id is smaller than the determination threshold Of as a result of the determination (step S272: No), the control unit 80 selects the integer number part value Ni as the threshold ThPix (step S273). On the other hand, if the integrated value Id is determined to be equal to or greater than the determination threshold Of (step S272: Yes), the control unit 80 subtracts the determination threshold Of from the integrated value Id (step S274) and selects the integer number part value Ni+1 as the threshold ThPix (step S275). In this way, in this embodiment, in the event that the integrated value Id corresponding to the positional error is accumulated to such an extent that the integrated value Id is carried up, that is, in the event that the integrated value Id is accumulated to reach the value of 1 of the count value CV, the threshold ThPix is incremented by one, whereby the accumulated positional errors can be reduced by such an extent as to correspond to the value of 1 of the count value CV by the traveling distance determination process (specifically, step S250) when it is executed next time. The step S274 reflects the positional error (the value of 1 of the count value CV) which is corrected by the threshold selection process executed this time and is executed in preparation for the threshold selection process to be executed next time. A value which is subtracted in step S274 is a quantity corresponding to the difference between the two thresholds.

Having set the threshold ThPix to either the value Ni or the value Ni+1, the control unit 80 calculates a clock signal off timing threshold ThClk (hereinafter, also referred to simply as a off timing threshold ThClk) and returns the process to the traveling distance determination process (step S276). The off timing threshold ThClk is a threshold for determining a timing at which the TDI clock signal falls. In this embodiment, the threshold ThClk is a value which is half the threshold ThPix. Namely, the threshold ThClk is set so that a high-level time and a low-level time are determined to have approximately the same length in a TDI clock generation process, which will be described later. According to this configuration, a rise and a fall of the TDI clock signal can be detected in the TDI clock camera 75 in an ensured fashion. The value which is half the threshold ThPix is converted to the nearest whole number by rounding or the like when the value includes decimal numbers.

Figure 8:
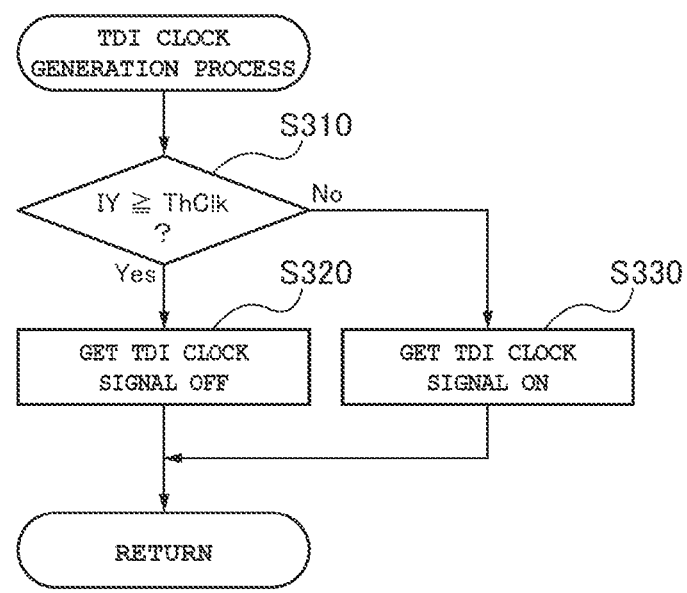
FIG. 8 is a flowchart showing a flow of TDI clock generation process.

FIG. 8 is a flowchart showing a flow of the TDI clock generation process (step S300 in FIG. 5). This process is a process of generating a TDI clock signal, in other words, a process of controlling a rising timing and a falling timing of a TDI clock signal. When this process is initiated, the control unit 80 first determines whether the traveling distance IY is equal to or greater than the off timing threshold ThClk (step S310).

If the traveling distance IY is determined to be equal to or greater than the off timing threshold ThClk as a result of the determination (step S310: Yes), the control unit 80 sets the TDI clock signal to OFF (an L level) (step S320). On the other hand, if the traveling distance IY is smaller than the threshold ThClk (step S310: No), the control unit 80 sets the TDI clock signal to ON (an H level) (step S330). In this way, having set the TDI clock signal to either ON or OFF, the control unit 80 returns the process to the traveling distance determination process.

Figure 9A:
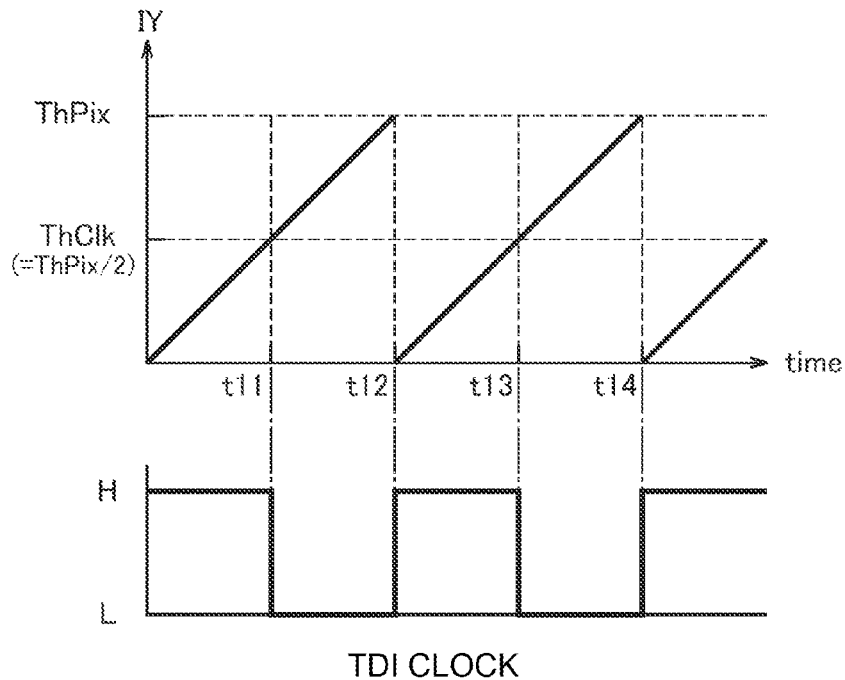
FIGS. 9A and 9B are diagrams depicting a relationship between a traveling distance of an inspection target object detected based on a count value of a laser interferometer and a TDI clock.
Figure 9B:
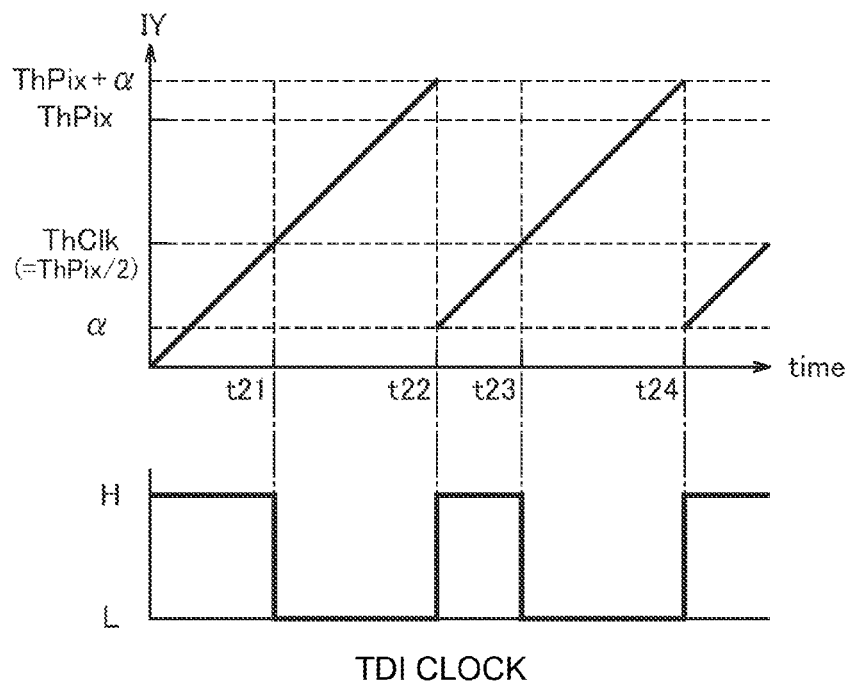

FIGS. 9A and 9B show schematically a relationship between the TDI clock signal outputted to the TDI camera 75 as a result of the TDI clock output process (refer to FIGS. 5 to 8) described above and the traveling distance IY. FIG. 9A shows a case where the determination in step S250 is made at the timing of the traveling distance IY=threshold ThPix. As shown in the figure, the TDI clock signal is held at the H level until a time t11 during which the traveling distance IY is smaller than the off timing threshold ThClk (step S310: No), while the TDI clock signal stays at the L level from the time t11 to a time t12 during which the traveling distance IY is equal to or greater than the off timing threshold ThClk (step S310: Yes). Then, when the traveling distance IY reaches the threshold ThPix (step S250: Yes), the traveling distance IY becomes a value of 0 (step S260), and the TDI clock signal is switched from the L lever to the H level (step S330). Thereafter, as with the period of time to the time t12, the TDI clock signal is switched from the H level to the L level at a time t13 when the traveling distance IY becomes equal to or greater than the off timing threshold ThClk, and is switched from the L level to the H level at a time t14 when the traveling distance IY reaches the threshold ThPix.

FIG. 9B shows a case where the determination in step S250 is made at the timing of traveling distance IY=threshold ThPix+α. As shown in the figure, the TDI clock signal remains at the H level until a time 21 during which the traveling distance IY is smaller than the off timing threshold ThClk, and is at the L level during a period of time from the time t21 to a time t22 during which the traveling distance IY becomes equal to or greater than the off timing threshold ThClk. Then, when the traveling distance IY reaches the threshold ThPix+α (that is, the determination in step S250 is executed), the traveling distance IY becomes a value of α (step S260), and the TDI clock signal is switched from the L level to the H level. Thereafter, as with the period of time to the time t22, the TDI clock signal is switched from the H level to the L level at a time 23 when the traveling distance IY becomes equal to or greater than the off timing threshold ThClk, and is switched from the L level to the H level at a time t24 when the traveling distance IY reaches the threshold ThPix+α.

According to the inspection system 5 which has been described heretofore, the two values (Ni, Ni+1) are used selectively as the threshold ThPix. Additionally, Ni (in the specific example described above, the value of 80) of the two values is smaller than the accurate traveling distance of the inspection target object which should correspond to the timing at which the TDI clock signal is generated, that is, the converted count value (in the specific example described above, the value of 80.8858), while Ni+1 (in the specific example described above, a value of 81) of the two values is greater than the converted count value. Because of this, an error between the threshold and the converted count value (the threshold—the converted count value) takes a minus value when Ni is used as the threshold ThPix and takes a plus value when Ni+1 is used as the threshold ThPix. Namely, using one threshold cancels part of the error caused when the other threshold is used. Consequently, compared with the case where one threshold is used in a fixed fashion (in this case, a constant positional error is accumulated at all times), the accumulation of positional errors which is caused by the fact that the count value CV acquired from the laser interferometer 58 for detecting the traveling distance of the wafer W is the integral value is restricted. As a result of this, it is possible to inspect the wafer W with good accuracy.

In addition, according to the inspection system 5, the decimal number part value Nd which is the value corresponding to the decimal number part of the converted count value is integrated the number of times the TDI clock signal is generated as the integrated value Id. Then, the value of the threshold ThPix is switched between Ni and Ni+1 based on the integrated value Id. Since the integrated value Id corresponds to an amount of accumulated positional errors, according to the configuration described above, the value of the threshold ThPix is switched before the positional errors are accumulated to the predetermined amount, thereby making it possible to reduce the accumulated positional errors.

In particular, in this embodiment, when the integrated value Id is smaller than the determination threshold Of, the first value Ni is selected as the threshold ThPix, while when the integrated value Id is equal to or greater than the determination threshold Of, the second value Ni+1, which is larger than the first value Ni, is selected as the threshold ThPix, and the value corresponding to the difference between the second value Ni+1 and the first value Ni (the determination threshold Of) is subtracted from the integrated value Id (step S274). Namely, the first value Ni is used as the threshold ThPix when the accumulated positional errors does not reach the amount corresponding to the determination threshold Of, while every time the accumulated positional errors exceeds the amount corresponding to the determination threshold Of, the second value Ni+1 is used in place of the first value Ni, whereby the accumulated positional errors are reduced. Consequently, since the accumulated positional errors are reduced every time the accumulated positional errors exceeds the amount corresponding to the predetermined value, there is no such situation where positional errors are accumulated to such an extent that the accumulated positional errors exceeds largely the predetermined amount.

Moreover, in this embodiment, the determination threshold Of is the value by which whether the integrated value Id is carried up by the integration (update) can be determined. The first value is the value of the integer number part of the converted count value (the integer number part value Ni). The second value is Ni+1 which is larger by the value of 1 than the first value. Consequently, since the positional error is reduced when the positional error is accumulated by the distance corresponding to the value of 1 of the count value CV of the laser interferometer 58, it is possible to hold the accumulation of positional errors to an extremely small value.

B. Second Embodiment

Figure 10:
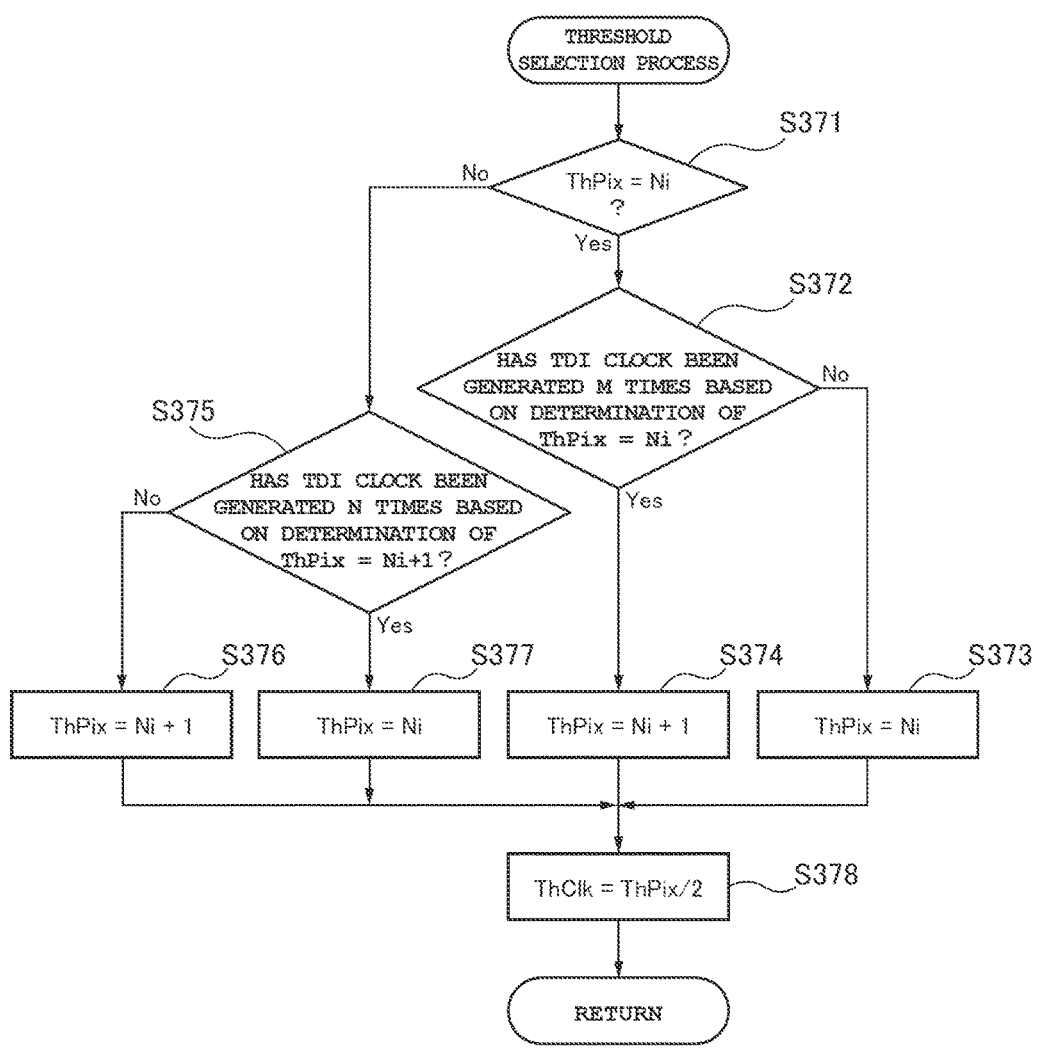
FIG. 10 is a flowchart showing a flow of threshold selection process of a second embodiment.

An inspection system as a second embodiment of the invention differs only in how to select a threshold ThPix from the first embodiment and remains the same as the first embodiment in the other features. Hereinafter, only features of the second embodiment which differ from those of the first embodiment will be described. FIG. 10 is a flowchart showing a flow of a threshold selection process as the second embodiment. When this process is initiated, a control unit 80 first determines whether a threshold ThPix is currently set to the integer number part value Ni (step S371).

If the threshold ThPix is determined to be set to the integer number part value Ni as a result of the determination (step S371: Yes), the control unit 80 determines whether the generation of a TDI clock signal based on the determination made in step S250 in which the integer number part value Ni is used as the threshold ThPix is executed M (M is a natural number) times continuously (step S372). If the TDI clock signal is determined not to be generated M times as a result of the determination (step S372: No), the control unit 80 selects the integer number part value Ni as the threshold ThPix (step S373). Namely, the threshold ThPix is maintained to be the integer number part value Ni. On the other hand, if the TDI clock signal is determined to be generated M times (step S372: Yes), the control unit 80 selects the integer number part value Ni+1 as the threshold ThPix (step S374). Namely, the threshold ThPix is switched from the integer number part value Ni to the integer number part value Ni+1.

On the other hand, if the threshold ThPix is not set to the integer number part value Ni (step S371: No), that is, if the threshold ThPix is set to the integer number part value Ni+1, the control unit 80 determines whether the generation of a TDI clock signal based on the determination made in step S250 in which the integer number part value Ni+1 is used as the threshold ThPix is executed N (N is a natural number) times continuously (step S375). If the TDI clock signal is determined not to be generated N times as a result of the determination (step S375: No), the control unit 80 selects the integer number part value Ni+1 as the threshold ThPix (step S376). Namely, the threshold ThPix is maintained to be the integer number part value Ni+1. On the other hand, if the TDI clock signal is determined to be generated N times (step S375: Yes), the control unit 80 selects the integer number part value Ni as the threshold ThPix (step S377). Namely, the threshold ThPix is switched from the integer number part value Ni+1 to the integer number part value Ni.

In this way, in case the threshold ThPix is set to either the value Ni or the value Ni+1, the control unit 80 calculates the off timing threshold ThClk and returns the process to the traveling distance determination process (step S378). The process in step S378 is the same process as the process in step S276.

According to the threshold selection process which has been described above, as with the first embodiment, since the two values Ni, Ni+1 are used as the threshold ThPix, the accumulation of positional errors which is caused by the fact that the count value CV is the integer value is restricted. In the first embodiment, while the control unit 80 is configured to select the value of the threshold ThPix based on the determination on whether the integrated value Id is carried up (step S272), the history of the integration of the integrated value depends on the resolution of the laser interferometer 58. In other words, a timing at which the integrated value Id is carried up can be grasped in advance based on the resolution of the laser interferometer 58. Consequently, in case values for M, N are determined based on the timing at which the integrated value Id is carried up, almost the same technical effect obtained by the first embodiment can be obtained by the second embodiment.

For example, in case the specified example shown in the First Embodiment the decimal number part value Nd=8858 is used, according to the threshold selection process (refer to FIG. 7) of the first embodiment, the integrated value Id changes in the following fashion from an initial value 0 to (10) 8580 (=9722+8858−10000) via (1) 8858(=0+8858), (2) 7716(=8858+8858−10000), (3) 6574(=7716+8858−10000), (4) 5432(=6574+8858−10000), (5) 4290(=5432+8858−10000), (6) 3148(=4290+8858−10000), (7) 2006 (=3148+8858−10000), (8) 864(=2006+8858−10000), (9) 9722(=864+8858). In the calculations above, the cases where the value of 10000 (the determination threshold Of) is subtracted (step S274) represent that the integrated value Id is carried up due to integration. Namely, in this example, the integrated value Id is not carried up only in the cases (1)

8858 and (9) 9722 and is carried up in the other cases. Additionally, although (1) 8858 and (10) 8580 are not completely the same, they are approximately the same in magnitude. Because of this, the integrated value Id can be generally regarded as changing in a cycle of (1) to (8). In case M and N are set as M=1, N=7 in consideration of the change or transition of the integrated value Id, the positional error can be corrected with accuracy which is close to the accuracy of the first embodiment.

According to the configuration of the second embodiment, the integrated value Id does not have to be calculated every time the TDI clock signal is generated, and the accumulation of positional errors can preferably be restricted by the simple logic. As an alternative example to the second embodiment, various forms can be adopted in which the value of the threshold ThPix is switched in a predetermined order associated with the transmission of a TDI clock signal. For example, the value Ni and the value Ni+1 may be selected alternately as the threshold ThPix. According to this configuration, although the correction accuracy with which the positional error is corrected is reduced compared with the embodiment described above, the accumulation of positional errors is restricted largely by the simpler configuration, compared with the configuration in which the constant threshold is used. Alternatively, a configuration may be adopted in which a threshold selection pattern (which may be configured as a table) which is associated with the transmission of a TDI clock signal is stored in the memory of the control unit 80, and after the control unit 80 transmits a Pth (P is an arbitrary natural number) TDI clock signal, the control unit 80 may refer to a threshold associated with the Pth transmission and select the referred threshold. By adopting this configuration, compared with the second embodiment, the level of correcting the positional error can be enhanced higher.

C. Modifications

C-1. Modification 1:

In the configuration described in the first embodiment in which whether the integrated value Id is carried up is determined, and if it is determined that the integrated value Id is carried up, the value Ni+1 is selected as the threshold ThPix, in place of determining whether the integrated value Id is carried up, a configuration may be adopted in which the integrated value Id is rounded to the nearest whole number. As this occurs, the value Ni+1 may be selected as the threshold ThPix when the integrated value Id is carried up as a result of the integrated value Id being rounded. Alternatively, in place of determining whether the integrated value Id is carried up, a configuration may be adopted in which the integrated value Id is compared with an arbitrary predetermined value. As this occurs, in case the integrated value Id is equal to or greater than the predetermined value, the value Ni+1 may be selected as the threshold ThPix.

C-2. Modification 2:

The integrated value Id may be integrated altogether every time the TDI clock signal is generated a predetermined number of times. For example, in case the integrated value Id is integrated every time the TDI clock signal is integrated Q (Q is an integer number equal to or greater than 2) times, in step S271, a value which is greater by Q times than the decimal number part value Nd may be added. As this occurs, two values may be set as values for the threshold ThPix in consideration of the value which is greater by Q times than the decimal number part value Nd. For example, in the event that a positional error of the order of a distance corresponding to three pixels is generated as a result of the integrated value Id being integrated four times, Ni and Ni+3 may be adopted for the threshold ThPix. In this way, by adopting the configuration in which in a stage where positional errors are accumulated to some extent, the accumulated positional errors are corrected altogether, it is possible to reduce processing load of the control unit.

C-3. Modification 3:

In the embodiments described heretofore, while the configurations are described mainly in which the accumulation of positional errors can be restricted with very good accuracy, the embodiments can be modified to an arbitrary configuration in which a plurality of thresholds are used selectively and which can restrict the accumulation of positional errors better than the configuration in which the single value is used as the threshold.

C-4. Modification 4:

In place of the TDI camera 75, various types of imaging units which can detect a quantity of secondary charged particles may be adopted. For example, a line sensor camera such as an EB (Electron Bombardment)-CCD, an I (Intensified)-CCD or the like. As this occurs, the control unit 80 may output an operation clock signal as a timing signal in place of the TDI clock signal.

Thus, while the several embodiments of the invention have been described heretofore, those embodiments are intended to facilitate the understanding of the invention and are not intended to limit the scope of the invention. The invention can be modified and/or improved without departing from the spirit and scope thereof, and equivalents thereof are, of course, included in the invention. In addition, it is possible to combine or omit arbitrarily the constituent elements described in claims and the specification within the scope where at least part of the problems described above can be solved and/or at least part of the advantages can be provided.

The present application claims the priority of the Japanese Patent Application No. 2014-078565 filed on Apr. 7, 2014 in Japan. This disclosure is incorporated herein by reference in its entirety.

What is claimed is:

1. A control unit for generating a timing signal for an imaging unit in an inspection system in which an image of an inspection target object is captured by the imaging unit while the inspection target object is caused to travel in a predetermined direction, the control unit comprising:
    a processor having a plurality of sections configured to execute steps of a control program;
    a storage memory medium configured to store the steps of the control program;
    a traveling distance determination section configured to detect a traveling distance of the inspection target object based on a count value acquired as an integer value from a laser interferometer provided in the inspection system for detecting a traveling distance of the inspection target object, and configured to determine whether the detected traveling distance reaches a threshold; and
    a timing signal generation section configured to generate a timing signal when it is determined that the detected traveling distance reaches the threshold, wherein
    the traveling distance determination section executes the determination by using a plurality of values selectively as the threshold, and
    wherein the traveling distance determination section is configured to integrate a decimal part corresponding value, which corresponds to a decimal part of a converted count value which results from converting a distance corresponding to one pixel of an image captured by the imaging unit into the count value of the laser interferometer in such a way as to include the decimal part, according to the number of times the timing signal is generated by the timing signal generating section, and configured to switch the threshold to be selected between the plurality of values based on the integrated decimal part corresponding value.

2. The control unit according to claim 1, wherein the traveling distance determination section is configured to select a first value of the plurality of values when the integrated decimal part corresponding value is smaller than a predetermined value, and is configured to select a second value of the plurality of values, the second value being larger than the first value, when the integrated decimal part corresponding value is equal to or larger than the predetermined value, and to subtract a value corresponding to a difference between the second value and the first value from the integrated decimal part corresponding value.

3. The control unit according to claim 2, wherein the plurality of values consist of the first value and the second value, wherein the predetermined value is a value by which whether the integrated decimal part corresponding value is carried up can be determined, the first value is a value corresponding to an integer part of the converted count value, and the second value is larger by a value of 1 than the first value.

4. The control unit according to claim 1, wherein the traveling distance determination section is configured to switch the threshold to be selected in a predetermined order which is associated with transmission of the timing signal by the timing signal generation section.

5. The control unit according to claim 4, wherein the traveling distance determination section is configured to switch the threshold from a first value to a second value, which differs from the first value, when the timing signal generation section generates the timing signal by a first predetermined number of times based on the first value as the threshold, and configured to switch the threshold from the second value to the first value when the timing signal generation section generates the timing signal by a second predetermined number of times based on the second value.

6. An inspection system comprising:
the control unit according to claim 1;
the imaging unit;
a traveling unit configured to hold the inspection target object to cause the inspection target object to travel in a predetermined direction; and
the laser interferometer.

7. A method for sending out a timing signal to an imaging unit in an inspection system in which an image of an inspection target object is captured by the imaging unit while the inspection target object is caused to travel in a predetermined direction, the method comprising:
detecting a traveling distance of the inspection target object based on a count value which is acquired as an integer value from a laser interferometer for detecting the traveling distance of the inspection target object to determine whether the detected traveling distance reaches a threshold; and
sending out the timing signal to the imaging unit when it is determined that the detected traveling distance reaches the threshold, wherein
the threshold is switched between a plurality of values selectively, and
wherein detecting the traveling distance includes integrating a decimal part corresponding value, which corresponds to a decimal part of a converted count value which results from converting a distance corresponding to one pixel of an image captured by the imaging unit into the count value of the laser interferometer in such a way as to include the decimal part, according to the number of times the timing signal is generated, and switching the threshold to be selected between the plurality of values based on the integrated decimal part corresponding value, and
wherein detecting the traveling distance includes integrating a decimal part corresponding value, which corresponds to a decimal part of a converted count value which results from converting a distance corresponding to one pixel of an image captured by the imaging unit into the count value of the laser interferometer in such a way as to include the decimal part, according to the number of times the timing signal is generated, and switching the threshold to be selected between the plurality of values based on the integrated decimal part corresponding value.

8. A control unit for generating a timing signal for an imaging unit in an inspection system in which an image of an inspection target object is captured by the imaging unit while the inspection target object is caused to travel in a predetermined direction, the control unit comprising:
a processor having a plurality of circuits configured to execute steps of a control program;
a storage memory medium configured to store the steps of the control program;
a traveling distance determination circuit for detecting a traveling distance of the inspection target object based on a count value acquired as an integer value from a laser interferometer provided in the inspection system for detecting a traveling distance of the inspection target object, and for determining whether the detected traveling distance reaches a first threshold; and
a timing signal generation circuit for generating a timing signal when it is determined that the detected traveling distance reaches the first threshold,
the traveling distance determination circuit executing the determination by using a plurality of values selectively as the first threshold,
the traveling distance determination circuit integrating a decimal part corresponding value, which corresponds to a decimal part of a converted count value which results from converting a distance corresponding to one pixel of an image captured by the imaging unit into the count value of the laser interferometer in such a way as to include the decimal part, according to the number of times the timing signal is generated by the timing signal generating circuit, and for switching the first threshold to be selected between the plurality of values based on the integrated decimal part corresponding value, and
the traveling distance determination circuit calculating a second threshold smaller than the first threshold based on the first threshold, the second threshold for determining a timing at which the timing signal to be terminated, the timing signal generation circuit terminating the timing signal when it is determined that the detected traveling distance reaches the second threshold.

9. The control unit according to claim 8, wherein the second threshold is a value which is half the first threshold.

* * * * *